United States Patent
Parker et al.

(10) Patent No.: US 7,018,948 B2
(45) Date of Patent: Mar. 28, 2006

(54) ACTIVATION AND REGENERATION OF A HYDRO-OXIDATION CATALYST

(75) Inventors: Deborah H. Parker, Racine, WI (US); Robert G. Bowman, Midland, MI (US); Howard W. Clark, Lake Jackson, TX (US); George E. Hartwell, Midland, MI (US); Alex Kuperman, Orinda, CA (US)

(73) Assignee: Dow Global Technologies Inc., Midland, MI (US)

( * ) Notice: Subject to any disclaimer, the term of this patent is extended or adjusted under 35 U.S.C. 154(b) by 415 days.

(21) Appl. No.: 10/148,804

(22) PCT Filed: Dec. 7, 2000

(86) PCT No.: PCT/US00/33385

§ 371 (c)(1),
(2), (4) Date: Sep. 30, 2002

(87) PCT Pub. No.: WO01/41926

PCT Pub. Date: Jun. 14, 2001

(65) Prior Publication Data

US 2003/0212283 A1 Nov. 13, 2003

Related U.S. Application Data

(60) Provisional application No. 60/169,862, filed on Dec. 9, 1999.

(51) Int. Cl.
*B01J 20/34* (2006.01)

(52) U.S. Cl. .......................... 502/38; 502/51
(58) Field of Classification Search .............. 502/38, 502/52
See application file for complete search history.

(56) References Cited

U.S. PATENT DOCUMENTS

| | | | |
|---|---|---|---|
| 5,183,789 A | * 2/1993 | Boyle | 502/52 |
| 5,254,512 A | * 10/1993 | Ueda et al. | 502/52 |
| 5,365,009 A | * 11/1994 | Uppal et al. | 585/722 |
| 5,620,935 A | 4/1997 | Thiele | |
| 5,623,090 A | * 4/1997 | Haruta et al. | 568/360 |
| 5,681,789 A | 10/1997 | Saxton et al. | |
| 5,798,313 A | 8/1998 | Carroll et al. | |
| 5,859,265 A | 1/1999 | Müller et al. | |
| 5,932,750 A | 8/1999 | Hayashi et al. | 549/523 |
| 5,939,569 A | 8/1999 | Jones et al. | 549/512 |
| 5,965,754 A | * 10/1999 | Clark et al. | 549/533 |
| 6,034,028 A | 3/2000 | Hayashi et al. | 502/243 |
| 6,063,941 A | 5/2000 | Gilbeau | 549/518 |
| 6,380,119 B1 | * 4/2002 | Grosch et al. | 502/49 |
| 6,518,441 B1 | * 2/2003 | Grosch et al. | 549/531 |

FOREIGN PATENT DOCUMENTS

| | | |
|---|---|---|
| DE | 09804712 A1 | 8/1999 |
| DE | 19804711 A1 | 8/1999 |
| EP | A1-0709360 | 5/1996 |
| EP | A1-0827779 | 3/1998 |
| EP | B1-0743094 | 7/2000 |
| EP | A1-1048660 | 11/2000 |
| GB | 2029719 | 3/1980 |
| WO | WO 97/25143 | 7/1997 |
| WO | WO 98/00413 | 1/1998 |
| WO | WO 98/00414 | 1/1998 |
| WO | WO 98/00415 | 1/1998 |
| WO | WO 99/00188 | 1/1999 |
| WO | WO 00/35893 | 6/2000 |
| WO | WO 00/59632 | 10/2000 |

\* cited by examiner

*Primary Examiner*—Stanley S. Silverman
*Assistant Examiner*—Jonas N. Strickland
(74) *Attorney, Agent, or Firm*—Marie F. Zuckerman

(57) ABSTRACT

A process of activating a fresh catalyst or regenerating a deactivated catalyst which is used in a hydro-oxidation process, preferably, the hydro-oxidation of an olefin in the presence of oxygen and hydrogen to an olefin oxide. The hydro-oxidation catalyst preferably comprises at least one metal selected from gold, silver, the platinum group metals, the lanthanide metals, and combinations thereof, incorporated onto a titanium-, vanadium-, or zirconium-containing support, more preferably, a titanium-containing support, such as titanium oxide or a titanosilicate. The activation or regeneration process involves contacting the fresh catalyst or the deactivated catalyst with ozone.

28 Claims, No Drawings

ACTIVATION AND REGENERATION OF A HYDRO-OXIDATION CATALYST

CROSS REFERENCE TO RELATED APPLICATION

This invention claims the benefit of U.S. Provisional Application Ser. No. 60/169,862, filed Dec. 9, 1999.

This invention was made with United States Government support under Award Number 70NANB5H1143 awarded by the National Institute of Standards and Technology The United States Government has certain rights in the invention.

BACKGROUND OF THE INVENTION

This invention pertains to a process of activating or regenerating a hydro-oxidation catalyst, preferably containing gold, or silver, or combinations thereof, dispersed on a titanium-containing support.

Hydro-oxidation catalysts find utility in hydro-oxidation processes, which involve the oxidation of organic compounds by oxygen in the presence of hydrogen. As one important use, olefins, such as propylene, can be hydro-oxidized directly with oxygen to olefin oxides, such as propylene oxide, in the presence of hydrogen and a hydro-oxidation catalyst, preferably containing gold, or silver, or combinations thereof, on a titanium-containing support. Olefin oxides, such as propylene oxide, are used inter alia to alkoxylate alcohols to form polyether polyols, such as polypropylene polyether polyols, which find significant utility in the manufacture of polyurethanes and synthetic elastomers. Another hydro-oxidation process involves the formation of useful oxygenated products, such as acetone and t-butanol, from alkanes in the presence of hydrogen, oxygen, and a hydro-oxidation catalyst.

The hydro-oxidation of olefins to olefin oxides has been described recently in several international patent publications. See, for example, WO 97/34692 and the following international patent publications of The Dow Chemical Company: WO 98/00413, WO 98/00414, WO 98/00415, which describe the use of catalysts containing gold deposited on a titanium-containing support for such processes. Likewise, international patent publication WO 99/00188 and U.S. provisional application 60/112,429, filed Dec. 16, 1998, corresponding to international patent publication WO 00/35893, also of The Dow Chemical Company, describe a catalyst containing silver or mixtures of silver and gold deposited on a titanium-containing support for the hydro-oxidation of olefins to olefin oxides. Other art, such as WO 96/02323, discloses a catalyst containing a platinum metal in at least two bond energy states deposited on titanium or vanadium silicalite for liquid phase olefin hydro-oxidations. Additional art, such as WO 97/25143, discloses a catalyst containing a lanthanide metal deposited on titanium or vanadium silicalite for liquid phase olefin hydro-oxidations. Still other art, for example EP-A1alkanes, such as propane, in the presence of hydrogen and oxygen and a hydro-oxidation catalyst to form useful oxidized products, such as acetone. Likewise, isobutane can be hydro-oxidized to t-butanol and acetone. Additional art, such as U.S. Pat. No. 5,939,569 describes a catalyst comprised of gold on zirconium-containing supports for hydro-oxidation.

A variety of catalytic supports are taught among the aforementioned references. For example, the titanium-containing supports are taught to include titanium dioxide, titanosilicates, titanium dispersed on silica (wherein the titanium exists as a disorganized phase), and likewise, titanium dispersed on certain metal silicates, as well as combinations and mixtures of the aforementioned materials. Optionally, as taught in international patent publication WO 98/00414, the catalyst can comprise one or more promoter metals selected, for example, from Group 1, Group 2, the lanthanide rare earth metals, and the actinide metals of the Periodic Table.

In a typical synthesis of the aforementioned hydro-oxidation catalysts, after the catalytic metals and optional promoter metal(s) are deposited onto the catalytic support, the composite is activated by calcining under air. or reducing under hydrogen, or by heating in an inert atmosphere, at a temperature between about 250° C. and about 800° C. for a time from about 1 hour to about 24 hours. Standard activation conditions operate at about 400° C. for 6 hours. The activated catalysts, particularly the catalysts comprising gold, silver, or combinations thereof, on a titanium-containing support, exhibit good olefin conversion and excellent selectivity to the olefin oxide, and may exhibit, depending upon the exact nature of the catalyst, long lifetime. Over time, however, these catalysts may lose some activity, and occasionally, may become sufficiently deactivated so as to render the catalyst impractical to use. At this stage of partial or full deactivation, the catalyst must be regenerated or replaced. As disclosed in WO 98/00414, for example, regeneration is taught to involve heating the deactivated catalyst for several hours under oxygen or hydrogen, optionally mixed with an inert diluent, such as, nitrogen or helium, at a temperature preferably between about 200° C. and about 400° C. Pressures ranging from atmospheric to superatmospheric can be employed. Alternatively, the deactivated catalyst can be regenerated in the presence of water, or a combination of water with oxygen or hydrogen, at similar temperatures and pressures.

The above-described activation and regeneration methods have drawbacks, first, in the length of time required, and secondly, in the high temperature required to effect the process. A high pressure may also be necessary. Typically, the activation or regeneration period consumes three to six hours. Disadvantageously, throughout this time the hydro-oxidation process is shut down. Usually, the activation and regeneration temperature significantly exceeds the hydro-oxidation process temperature, which is typically greater than about 70° C. and less than about 225° C. Accordingly, the catalyst must be heated up to the activation or regeneration temperature, and when the activation or regeneration is complete, cooled down to the operating temperature of the hydro-oxidation process. This temperature cycling consumes valuable time, during which the hydro-oxidation process remains inoperative. As an added disadvantage, the higher activation and regeneration temperature requires an input of heat and energy. Moreover, the reactor must be constructed to withstand the higher regeneration temperature and to permit cycling between the hydro-oxidation process temperature and the higher regeneration temperature. Most disadvantageously, repeated cycling through the higher activation and regeneration temperature may damage the structure of the catalyst support and/or may result in damage to the metals incorporated thereon. With each regeneration cycle a percentage of the catalyst activity may be irretrievably lost until at some point of sudden or accumulated large loss, the catalyst must be replaced.

In view of the above, it would be desirable to discover an activation and regeneration method which is efficiently accomplished in a short period of time at a temperature and pressure which are closely similar to the operating conditions of the hydro-oxidation process. Such an activation and regeneration method would reduce the heat and energy demands made on the overall process and would reduce shut-down time on the hydro-oxidation process. More desirably, since there would be essentially no recycling through higher temperature zones, the process would minimize damage to the catalytic support and damage to the catalytic metals, thereby prolonging catalyst lifetime. It would be even more desirable if the activation and regeneration method could be accomplished without introducing liquid activation or regeneration agents into the reactor, because the removal of liquids would complicate and increase the cost of the method.

SUMMARY OF THE INVENTION

This invention is a novel process of activating or regenerating a catalyst which is used in hydro-oxidation processes. The hydro-oxidation process involves contacting a hydrocarbon with oxygen in the presence of hydrogen and the hydro-oxidation catalyst to form an oxidized product, preferably, a partially oxidized hydrocarbon. The term "partially oxidized hydrocarbon" implies that the product contains carbon, hydrogen, and oxygen, as opposed to containing only carbon and oxygen, as illustrated by deep oxidation products, such as, carbon monoxide and carbon dioxide. More preferably, the hydro-oxidation process involves contacting an olefin or mixture of olefins with oxygen in the presence of hydrogen and in the presence of the hydro-oxidation catalyst under process conditions sufficient to prepare useful oxidized products, for example, the corresponding olefin oxide or mixture of olefin oxides. In another preferred embodiment, alkanes can be hydro-oxidized to useful products, such as, alcohols and ketones.

The novel activation or regeneration process of this invention comprises contacting a fresh or deactivated hydro-oxidation catalyst with an ozone-containing stream under process conditions sufficient to activate the fresh catalyst or regenerate, at least in part, the deactivated catalyst. For the purposes of this invention, the "fresh catalyst" is defined as an unused catalyst, preferably, a catalyst in its "as-synthesized" form. For the purposes of this invention, a "deactivated catalyst" is defined as a catalyst which exhibits partial or full loss of activity in the hydro-oxidation process, as compared under similar process conditions with the activity of the fresh catalyst.

The process of this invention efficiently activates or regenerates hydro-oxidation catalysts, preferably hydro-oxidation catalysts comprising gold, or silver, or combinations of gold and silver, and optionally, at least one promoter metal, dispersed on a titanium-containing support. The activation/regeneration process of this invention can be accomplished with gas phase reagents, which are easily removed from the reactor. No liquid phase reagents are required, whose removal would complicate the process and increase costs. The activation/regeneration process of this invention can be advantageously conducted at temperatures and pressures similar to or lower than the temperature of the hydro-oxidation process. Accordingly, the activation/regeneration process of this invention essentially does not require an additional input of heat or energy beyond that required for the hydro-oxidation process itself, and may even consume less energy. More advantageously, the activation and regeneration method of this invention substantially avoids repeated thermal cycling of the catalyst between a lower hydro-oxidation operating temperature and a higher activation or regeneration temperature. Thus, damage to the support and damage to the metals incorporated thereon are significantly reduced, and there is less wear on the reactor. Moreover, the reactor need only be constructed to accommodate the hydro-oxidation process temperature; no special construction for withstanding higher regeneration temperatures is required. As another advantage, the process of the invention can be accomplished over a shorter period of time, as compared with prior art activation and regeneration methods. The shorter activation and regeneration periods, together with the lower temperature and pressure, result in longer catalyst lifetime, shorter down-time periods, and higher productivity for the hydro-oxidation process.

DETAILED DESCRIPTION OF THE INVENTION

This invention provides a process of activating or regenerating a catalyst which is useful in hydro-oxidation processes, preferably, the hydro-oxidation of olefins to olefin oxides. As noted hereinbefore, the hydro-oxidation process generally involves contacting a hydrocarbon with oxygen in the presence of hydrogen and a hydro-oxidation catalyst to form an oxidized product, preferably, a partially oxidized hydrocarbon. More preferably, the hydro-oxidation process involves contacting an olefin or mixture of olefins with oxygen in the presence of hydrogen and the hydro-oxidation catalyst to form the corresponding olefin oxide or mixture of olefin oxides. The contacting is effected under hydro-oxidation process conditions sufficient to prepare the oxidized product, preferably, the olefin oxide or mixture thereof.

The hydro-oxidation catalyst can be any catalyst which catalyzes the oxidation of an organic compound with oxygen in the presence of hydrogen. Preferably, the hydro-oxidation catalyst comprises one or more metals selected from gold, silver, the platinum group metals, the lanthanide metals, and combinations thereof, deposited on a support. The term "platinum group metals," as used herein, includes ruthenium, rhodium, palladium, osmium, iridium, and platinum. Preferably, the support is a titanium-containing, a vanadium-containing, or a zirconium-containing support. More preferably, the hydro-oxidation catalyst comprises gold, or silver, or a combination of silver and gold, dispersed on a titanium-containing support. Optionally, the hydro-oxidation catalyst may further comprise at least one promoter metal, which is described hereinafter.

The novel activation or regeneration process of this invention comprises contacting a fresh or deactivated hydro-oxidation catalyst with an ozone-containing stream under process conditions sufficient to activate the fresh catalyst or regenerate, at least in part, the deactivated catalyst. As noted hereinbefore, the "fresh catalyst" is defined as a catalyst in an "as-synthesized" form, that is, a catalyst obtained from its synthesis mixture with no prior use in the hydro-oxidation process. Catalytic activity can vary with many parameters, among them, the exact form of the catalytic support, the exact form of the catalytic metal(s) and optional promoter metal(s), and the specific hydro-oxidation process involved. Accordingly, it is difficult to state in general terms what activity defines the "activated" state for a specific fresh hydro-oxidation catalyst. One skilled in the art will be able to judge whether a particular fresh catalyst species has been activated, for example, by observing whether the catalyst treated by the method of the invention is capable of converting reactants in the hydro-oxidation process to oxidized products. As a guideline, but without being bound by such a result, in the hydro-oxidation of an olefin, an activated catalyst typically exhibits an olefin conversion of at least about 0.05 mole percent and a selectivity to olefin oxide of at least about 60 mole percent. For the purposes of this invention, the "deactivated catalyst" is defined as a catalyst which exhibits a partial or full loss of activity on use in the hydro-oxidation process, as compared with the activity of the fresh catalyst under similar process conditions.

The preferred hydro-oxidation catalyst which is beneficially employed in the process of this invention comprises at least one catalytic metal selected from gold, silver, the platinum group metals, the lanthanide metals, and combinations thereof, on a support selected from titanium-containing, vanadium-containing, and zirconium-containing supports. The more preferred catalyst which is beneficially employed in the process of this invention comprises gold, or silver, or a combination of gold and silver, dispersed on a titanium-containing support. Optionally, the catalyst can further comprise one or more promoter metals. Preferably, the promoter metal is selected from Group 1, Group 2, the platinum group metals, the rare earth lanthanides, and the actinide metals of the Periodic Table, as referenced in the *CRC Handbook of Chemistry and Physics*, 75$^{th}$ ed., CRC Press, 1994. (The platinum group metals and the lanthanide metals may act as promoters, for example, when combined with gold and/or silver. Alternatively, the platinum group metals and the lanthanide metals may act as the primary catalytic metals, for example, when deposited on titanium or vanadium silicalite.) The oxidation state of the catalytic metals, preferably gold and/or silver, or any promoter metal (s) can be any oxidation state or combination of oxidation states, including zerovalent and positive oxidation states, as determined by modern analytical methods, provided that the catalyst obtained therefrom is capable of catalyzing the hydro-oxidation process, preferably, the olefin hydro-oxidation process described herein. Metallic particles may or may not be present. If metallic particles are present in the catalyst, there is no limitation on their particle size. Surprisingly, the ozone treatment of this invention reactivates the aforementioned preferred catalyst species in olefin hydro-oxidation processes without significantly reducing olefin conversion and olefin oxide selectivity, and without significantly increasing water and by-product formation.

The total loading of catalytic metals in the hydro-oxidation catalyst can be any quantity which yields an active catalyst in the hydro-oxidation process. Generally, the total loading of catalytic metals on the hydro-oxidation catalyst, preferably the total gold and silver loading, is at least about 0.005, preferably, at least about 0.01, and more preferably at least about 0.03 weight percent, based on the total weight of the catalyst. Generally, the total loading of catalytic metals, preferably the total gold and silver loading, is less than about 20, preferably, less than about 10, and more preferably, less than about 5.0 weight percent, based on the total weight of the catalyst. In another preferred embodiment, the process is advantageously conducted at a total loading, preferably a total gold and silver loading, of less than about 0.5 weight percent, more preferably, less than about 0.1 weight percent. The catalytic support may be any material on which the catalytic metal(s) and optional promoter metal(s) can be incorporated and which results in an active hydro-oxidation catalyst. The preferred support is a titanium-containing support, which may take a variety of forms. Typically, the titanium exists essentially as non-metallic titanium. The titanium-containing supports described hereinafter are illustrative of those which can be used in the process of this invention; however, the examples provided should not be construed to be limiting of the invention in any manner. One skilled in the art may recognize other supports which could be used equivalently in the process of this invention. For example, combinations and mixtures of the supports described hereinafter can be employed.

Amorphous and crystalline titanium dioxide are beneficially employed as the titanium-containing support. The crystalline phases of titanium dioxide include anatase, rutile, and brookite. Composites and deposits of these phases on various supports, such as silicas, aluminas, and aluminosilicates, are also suitably employed.

Crystalline and amorphous titanosilicates, preferably those which are porous, are beneficially employed as the support. Non-limiting examples of suitable porous titanosilicates include porous amorphous titanosilicates; porous layered titanosilicates; and crystalline microporous titanosilicates, such as titanium silicalite-1 (TS-1), titanium silicalite-2 (TS-2), titanosilicate beta (Ti-beta), titanosilicate ZSM-12 (Ti-ZSM-12), and titanosilicate ZSM-48 (Ti-ZSM-48); as well as mesoporous titanosilicates, such as, Ti-MCM41. Many references describing the preparation and characterization of the aforementioned titanosilicates are known to those skilled in the art. A relevant selection of references can be found, for example, in international patent publication WO 98/00414, incorporated herein by reference. The silicon to titanium atomic ratio of the titanosilicate can vary broadly, for example, from equal to or greater than about 5/1 to equal to or less than about 200/1.

As another example, titanium dispersed on silica can be beneficially employed as the titanium-containing support. This support can be obtained commercially or prepared by the methods described in international patent publication WO 98/00415, incorporated herein by reference. The titanium loading on the silica can be any which gives rise to an active catalyst in the hydro-oxidation process. Typically, the titanium loading is greater than about 0.02 weight percent, preferably, greater than about 0.1 weight percent, based on the weight of the silica. Typically, the titanium loading is less than about 20 weight percent, and preferably less than about 10 weight percent, based on the weight of the silica. In a preferred embodiment, the titanium ions are dispersed substantially in a disorganized phase over the surface of the silica. The disorganized titanium phase can be distinguished from bulk crystalline titanium dioxide by one or more modern analytical techniques, including for example, high resolution transmission electron microscopy (HR-TEM) and Raman spectroscopy. Ultraviolet-visible diffuse reflectance spectroscopy (UV-VIS DRS) and titanium K-edge X-Ray Absorption Near Edge Structure (XANES) spectroscopy may also be useful in the identification of the disorganized phase. These techniques are described in more detail in international patent publication WO 98/00415, incorporated herein by reference.

Likewise, titanium dispersed on a promoter metal silicate can be beneficially employed as the titanium-containing support. Stoichiometric and non-stoichiometric promoter metal silicates can be used, as can amorphous and crystalline promoter metal silicates. Preferred promoter metal silicates include the silicates of Group 1, Group 2, the lanthanide rare earth metals, and the actinide metals, and combinations thereof. Regarding this type of support, reference is again made to international patent publication WO 98/00414, incorporated herein by reference.

In a more preferred embodiment, the titanium-containing support comprises extra-framework or non-framework titanium bonded to a support. The support can be any material to which titanium can be affixed, including, for example, silicas, aluminas, metallosilicates, such as aluminosilicates and titanosilicates; and promoter metal silicates, most preferably, the silicates of Groups 1 and 2, the lanthanide rare earths, and the actinide elements. This type of support may also be crystalline, quasi-crystalline, or amorphous; and may contain a regular or irregular arrangement of non-connecting or interconnecting micropores (pore diameter from about 4 Å to about 20 Å) and/or mesopores (pore diameter from greater than about 20 Å to about 500 Å). There is no limitation on the manner in which the titanium is bonded to the support. Any type of bonding ranging from very weak interactions, like Van der Waals forces, to fully anchored (or grafted) bonds, are acceptable. Deposited, dispersed, and grafted models are all included in this form of the support. Examples of extra-framework or grafted titanium-containing supports include, without limitation, titania (or other discrete titanium-containing compositions) occluded onto a support material, such as, a silicate framework; titanium deposited as ions or ion clusters onto a support material, such as a refractory oxide or a metallosilicate; and titanium, preferably non-metallic titanium, grafted onto a framework structure, such as titanium grafted onto a silicate framework. The more preferred specie comprises titanium grafted onto a titanosilicate framework, most preferably, titanium grafted onto a titanosilicate framework of an MFI crystallographic structure. The titanium loading and the silicon to titanium atomic ratio of this type of support may be similar to those values presented hereinabove in connection with the titanium dispersed on silica support. For a method of preparing the extra-framework or grafted titanium-containing support, reference is made to U.S. provisional application Ser. No. 60/128,394, filed Apr. 8, 1999, corresponding to international patent publication WO 00/59632, incorporated herein by reference.

Stoichiometric and non-stoichiometric promoter metal titanates can also be beneficially employed as the catalyst support. The promoter metal titanates can be crystalline or amorphous. Non-limiting examples of these include the titanates of Group 1, Group 2, and the lanthanide and actinide metals of the Periodic Table.

By analogy to the above description, suitable vanadium-containing supports include vanadium oxides, vanadosilicates, vanadium dispersed on silica or promoter metal silicates, and extra-framework or non-framework vanadium bonded or grafted onto a support. Suitable zirconium-containing supports include zirconia and zirconium dispersed or grafted onto a support, such as, silica or a promoter metal silicate.

The catalytic support, preferably the titanium-containing supports described hereinabove, may be shaped into any form suitable for catalyst particles, for example, beads, pellets, spheres, honeycombs, monoliths, and films. Optionally, any of these supports can be extruded with, bound to, or supported on a second support for the purpose of binding together the catalyst particles and/or improving the catalyst's strength or attrition resistance. The second support is typically inert in the process and need not contain titanium. Suitable secondary supports include carbon, refractory oxides, such as, silica and alumina; aluminosilicates; ceramics, including ceramic carbides and nitrides; as well as any metallic support. Generally, the quantity of second support ranges from about 0 to about 95 weight percent, based on the combined weight of the catalyst and second support.

The catalytic metals, preferably the gold and silver components, can be deposited on, or supported on, and/or incorporated in the catalytic support by any method known in the art which provides for an active and selective hydro-oxidation catalyst. Non-limiting examples of known preparation methods include impregnation, ion-exchange, and deposition by precipitation. In one method of preparing a gold catalyst, the support is contacted with an aqueous solution of a soluble gold compound at a temperature and pH sufficient to precipitate the gold compound onto the support. Non-aqueous solutions can also be employed. For aqueous solutions, any water soluble gold compound can be used, such as chloroauric acid, sodium chloroaurate, potassium chloroaurate, gold cyanide, potassium gold cyanide, and diethylamine auric acid trichloride. Typically, the molarity of the soluble gold compound ranges from about 0.001 M to the saturation point of the soluble compound, preferably, from about 0.005 M to about 0.5 M. In depositing gold, the pH of the aqueous solution is adjusted to between about 5 and about 11, preferably, between about 6 and about 9, with any suitable base, such as Group 1 metal hydroxides or carbonates, preferably sodium hydroxide, sodium carbonate, potassium carbonate, cesium hydroxide, and cesium carbonate. The desired quantity of support is added to the solution, or vice versa; and if necessary or desired, the pH is again adjusted. Thereafter, the mixture is stirred under air at a temperature between about 20° C. and about 80° C. for a time ranging from about 1 hour to about 24 hours. At the end of this period, the solids are recovered, optionally washed with water, with preferably no more than about 100 ml wash liquid per gram composite. The water may optionally contain one or more promoter metal salts preferably at a pH between about 5 and about 11. Thereafter, the solids may be dried under air at a temperature between about 80° C. and about 120° C. to recover the as-synthesized catalyst. Optionally, the as-synthesized catalyst may be calcined under air, or calcined in a reducing atmosphere, such as hydrogen, or heated in an inert atmosphere, such as nitrogen, at a temperature between about 250° C. and about 800° C. for a time from about 1 to 24 hours.

One method of preparing silver catalysts is by impregnating a soluble silver compound onto the selected catalyst support, such as the titanium-containing support. Aqueous and non-aqueous silver solutions can be used. Any soluble silver compound can be employed, for example, with aqueous solutions, silver nitrate, silver acetate, silver oxalate, and the like, are suitable. Typically, the molarity of the soluble silver compound ranges from about 0.001 M to the saturation point of the soluble compound, preferably, from about 0.005 M to about 0.5 M. The impregnation temperature varies generally from about ambient, taken as 20° C., to about 100° C., at atmospheric pressure. The impregnated support is optionally washed with water, with preferably no more than about 100 ml wash liquid per gram composite. The water may optionally contain one or more promoter metal salts preferably at a pH between about 5 and about 11. Thereafter, the solids may be dried under air at a temperature between about 80° C. and about 120° C. to recover the as-synthesized catalyst. Optionally, the as-synthesized catalyst may be calcined under air, or calcined in a reducing atmosphere, such as hydrogen, or heated in an inert atmosphere, such as nitrogen, at a temperature between about 250° C. and al)out 800° C. for a time from about 1 to 24 hours. The aforementioned deposition methods for gold and silver can be conducted sequentially to obtain a catalyst comprising both gold and silver.

The above-described preparation methods are for illustrative purposes only. In practice, there is no limitation on the catalyst preparation method. For example, the hydro-oxidation catalyst containing gold may be prepared by impregnation, as well as the deposition method described hereinabove; while the silver catalyst can be prepared by deposition, as well as the impregnation method described hereinabove. Hydro-oxidation catalysts comprising metals other than gold and silver, such as the platinum group metals or lanthanide metals, may be prepared in analogous fashion to those methods described hereinbefore. Impregnation methods, which are well known in the art, may be preferentially employed.

As a further option, the hydro-oxidation catalyst may contain at least one promoter metal, defined as any metal ion having a valence between +1 and +7 which enhances the productivity of the catalyst in the hydro-oxidation process. Factors contributing to increased productivity include, for example, increased conversion of reactants, such as the olefin; increased selectivity to desired products, such as the olefin oxide; decreased production of by-products, such as water in the olefin hydro-oxidation process; and increased catalyst lifetime. Non-limiting examples of suitable promoter metals, particularly for the olefin hydro-oxidation process, include the metals of Groups 1 through 12 of the Periodic Table, as well as the rare earth lanthanides and actinides, previously referenced in the *CRC Handbook of Chemistry and Physics*. Preferably, the promoter metal is selected from Group 1 metals of the Periodic Table including lithium, sodium, potassium, rubidium, and cesium; from Group 2 metals, including beryllium, magnesium, calcium, strontium, and barium; from the platinum group metals, including ruthenium, rhodium, palladium, rhenium, osmium, and iridium; from the lanthanide rare earth metals, including cerium, praseodymium, neodymium, promethium, samarium, europium, gadolinium, terbium, dysprosium, holmium, erbium, thulium, ytterbium, and lutetium; and the actinide metals, specifically, thorium and uranium. More preferably, the promoter metal is magnesium. calcium, barium, erbium, lutetium, lithium, sodium, potassium, rubidium, cesium, or a combination thereof.

The total quantity of promoter metal(s) added to the support typically is greater than about 0.0001 , preferably, greater than about 0.01, and more preferably, greater than about 0.15 weight percent, based on the total weight of the catalyst. The total quantity of promoter metal(s) deposited on the support is generally less than about 20, preferably, less than about 15, and more preferably, less than about 10 weight percent, based on the total weight of the catalyst. Those skilled in the art will recognize that when a promoter metal titanate or silicate is employed, the weight percentage of promoter metal may be much higher, for example, as high as about 80 weight percent.

Typically, the promoter metal is added from an aqueous or organic solution containing a soluble promoter metal salt, such as, a promoter metal nitrate, carboxylate, or halide. Ordinarily, the support is contacted with the solution of the promoter metal salt under conditions which are similar to those used for contacting the support with the gold or silver solution. In the preferred catalyst comprising gold, or silver, or a combination thereof, on a titanium-containing support, the promoter can be added before, after, or during the titanium deposition. Alternatively, the promoter can be added before, after, or during the gold or silver deposition. After the promoter metal is added, washing is optional, and if done to excess, can leach at least a portion of the promoter metal out of the catalyst. Afterwards, calcination under air, or heating under a reducing atmosphere, or heating in an inert gas is optional, as described hereinabove in connection with the gold and silver incorporations.

The activation or regeneration process of this invention is conducted in any reactor suitably designed for a liquid or gas phase hydro-oxidation process. Suitable reactors include batch, fixed-bed, transport bed, fluidized bed, moving bed, shell and tube, and trickle bed reactors, as well as continuous and intermittent flow and swing reactor designs. In a typical procedure, the fresh catalyst is loaded into the reactor and heated to the activation temperature under a flow of oxygen, air, or an inert gas, and then an ozone-containing stream is passed over the catalyst for a time sufficient to effect activation. The regeneration process involves first shutting down the hydro-oxidation process, then if need be, adjusting the temperature of the reactor to the desired regeneration temperature, and then contacting the deactivated catalyst with the ozone-containing stream for a time sufficient to effect regeneration.

In theory, pure ozone can be employed; although in practice, it is preferred to expose the catalyst to a gaseous stream containing less than about 20 volume percent ozone, and more preferably, less than about 10 volume percent ozone. Preferably, the ozone stream contains greater than about 0.05 volume percent ozone, and more preferably, greater than about 0.1 volume percent ozone. The balance of the gas stream may be any diluent gas or mixture of diluent gases which is substantially unreactive with ozone, such as oxygen, nitrogen, air, argon, helium, water, and carbon dioxide. Methods of generating ozone are well known, including, for example, UV irradiation of air or oxygen, as well as corona discharge techniques. Ozone generators are commercially available. The use of oxygen or oxygen-enriched air as a feed to an ozone generator may be used in order to attain the desired ozone concentration.

When the method of the invention is used to regenerate catalysts which are used in liquid phase hydro-oxidation processes, then it may be preferable to remove the liquid phase prior to the addition of the ozone-containing stream. The method of this invention, itself, may be conducted in the liquid phase, provided that the liquid phase is non-reactive with respect to ozone and the hydro-oxidation catalyst. Preferentially, the method of this invention is carried out in a gas phase.

Any gas hourly space velocity of the ozone-containing stream can be beneficially employed, providing the catalyst is activated or regenerated. The gas hourly space velocity of the ozone-containing stream generally is greater than about 0.1 milliliter per milliliter catalyst per hour ($h^{-1}$), and preferably, greater than about 10 $h^{-1}$. The gas hourly space velocity of the ozone-containing stream generally is less than about 1,000 $h^{-1}$, and preferably, less than about 500 $h^{-1}$.

The temperature of the activation or regeneration process typically is greater than ambient temperature (taken as about 20° C.), and preferably, is greater than about 70° C. The activation or regeneration temperature is typically less than about 250° C., and preferably, less than about 170° C. The activation or regeneration cycle is typically greater than about 5 minutes, and preferably, greater than about 15 minutes. Typically, the activation or regeneration cycle is less than about 6 hours, and preferably, less than about 3 hours. The duration of the regeneration cycle may also depend upon the reactor configuration, catalyst volume, and hydro-oxidation process conditions. The total pressure of the activation or regeneration process can vary broadly from subatmospheric to superatmospheric pressures; but preferably, the total pressure is greater than about 7 psia (48 kPa) and less than about 100 psia (690 kPa).

The preferred hydro-oxidation process which directly oxidizes an olefin with oxygen in the presence of hydrogen to an olefin oxide has been described in the prior art. Basic aspects of the olefin hydro-oxidation process are summarized hereinafter for the sake of thoroughness; but for a more detailed discussion, see, for example, international patent publications WO 98/00413, WO 98/00414, WO 98/00415, and WO 97/34692, incorporated herein by reference.

Any olefin containing three or more carbon atoms, or mixture of such olefins, can be employed in the hydro-oxidation process, provided that the corresponding olefin oxide is produced. Examples of olefins which are suitably employed include, without limitation, propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methyl pentene, ethyl butene, heptene, methyl hexene, ethylpentene, propylbutene, the octenes, including preferably 1-octene, and other higher analogues of these; as well as butadiene, cyclopentadiene, dicyclopentadiene, styrene, α-methylstyrene, divinylbenzene, allyl chloride, allyl alcohol, allyl ether, allyl ethyl ether, allyl butyrate, allyl acetate, allyl benzene, allyl phenyl ether, allyl propyl ether, and allyl anisole. Preferably, the olefin is a $C_{3-12}$ olefin, more preferably, a $C_{3-8}$ olefin. Most preferably, the olefin is propylene.

The quantities of olefin, hydrogen, oxygen, and any optional diluent in the hydro-oxidation feedstream can vary over a wide range, provided that the corresponding olefin oxide is produced. Typically, the quantity of olefin in the hydro-oxidation feedstream is greater than about 1, preferably, greater than about 10, and more preferably, greater than about 20 mole percent, based on the total moles of olefin, oxygen, hydrogen, and optional diluent. Typically, the quantity of olefin is less than about 99, preferably, less than about 85, and more preferably, less than about 70 mole percent, based on the total moles of olefin, oxygen, hydrogen, and optional diluent. Preferably, the quantity of oxygen in the hydro-oxidation feedstream is greater than about 0.01, most preferably greater than about 5 mole percent, based on the total moles of olefin, hydrogen, oxygen, and optional diluent. Preferably, the quantity of oxygen in the hydro-oxidation feedstream is less than about 30, more preferably less than about 20 mole percent, based on the total moles of olefin, oxygen, hydrogen, and optional diluent. Suitable quantities of hydrogen are typically greater than about 0.01, preferably, greater than about 0.1, and more preferably, greater than about 3 mole percent, based on the total moles of olefin, hydrogen, oxygen, and optional diluent. Suitable quantities of hydrogen are typically less than about 50, preferably, less than about 30, and more preferably, less than about 20 mole percent, based on the total moles of olefin, hydrogen, oxygen, and optional diluent.

In addition to the above reagents, it may be desirable to employ a diluent with the reactants. The diluent can be any gas or liquid which does not inhibit the hydro-oxidation process. Suitable gaseous diluents include, diluents include aliphatic alcohols, preferably $C_{1-10}$ aliphatic alcohols, such as methanol and t-butanol: chlorinated aliphatic alcohols, preferably $C_{1-10}$ chlorinated alkanols, such as chloropropanol, chlorinated aromatics, preferably chlorinated benzenes, such as chlorobenzene and dichlorobenzene; as well as liquid polyethers, polyesters, and polyalcohols. If a diluent is used, the amount of diluent is typically greater than about 0, preferably greater than about 0.1, and more preferably, greater than about 15 mole percent, based on the total moles of olefin, oxygen, hydrogen, and optional diluent. The amount of diluent is typically less than about 90, preferably, less than about 80, and more preferably, less than about 70 mole percent, based on the total moles of olefin, oxygen, hydrogen, and diluent.

The olefin hydro-oxidation process is conducted at a temperature typically greater than about ambient, taken as 20° C., preferably, greater than about 70° C., more preferably greater than about 130° C. Usually, the olefin hydro-oxidation process is conducted at a temperature less than about 250° C., preferably less than about 225° C., more preferably, less than about 210° C. Preferably, the pressure of the olefin hydro-oxidation process ranges from about atmospheric to about 400 psig (2758 kPa), more preferably, from about 150 psig (1034 kPa) to about 250 psig (1724 kPa). In flow reactors the gas hourly space velocity (GHSV) of the olefin is typically greater than about 10 ml olefin per ml catalyst per hour ($h^{-1}$), preferably greater than about 100 $h^{-1}$, and more preferably, greater than about 1,000 $h^{-1}$. Typically, the GHSV of the olefin is less than about 50,000 $h^{-1}$, preferably, less than about 35,000 $h^{-1}$, and more preferably, less than about 20,000 $h^{-1}$. Likewise, for liquid phase continuous processes, the weight hourly space velocity (WHSV) of the olefin component can vary over a wide range, but typically is greater than about 0.01 g olefin per g catalyst per hour ($h^{-1}$), preferably, greater than about 0.05 $h^{-1}$, and more preferably, greater than about 0.1 $h^{-1}$. Typically, the WHSV of the olefin is less than about 100 $h^{-1}$, preferably, less than about 50 $h^{-1}$, and more preferably, less than about 20 $h^{-1}$. The gas and weight hourly space velocities of the oxygen, hydrogen, and diluent components can be determined from the space velocity of the olefin taking into account the relative molar ratios desired.

The hydro-oxidation process conditions, described hereinabove with respect to olefin hydro-oxidation, may be generally applied to other types of hydrocarbons that are suitable for hydro-oxidation processes. Alkanes, for example, may be substituted for olefins in the aforementioned description of hydro-oxidation processes. The hydro-oxidation of alkanes typically yields alcohols or ketones.

The invention will be further clarified by a consideration of the following examples, which are intended to be purely exemplary of the use of the invention. Other embodiments of the invention will be apparent to those skilled in the art from a consideration of this specification or practice of the invention as disclosed herein.

COMPARATIVE EXPERIMENT 1

(CE-1) Regeneration by Method of the Prior Art

A hydro-oxidation catalyst comprising gold dispersed on a support comprising titania on silica was prepared in a similar manner to that described in Example 1 of international patent publication WO 97/34692, Example 1 being incorporated herein by reference. One difference, however, is that the catalyst preparation herein did not involve extensive washing after gold deposition at pH 8.8. In contrast, Example 1 of WO 97/34692 does not specify the quantity of water used in washing, while other examples in WO 97/34692 use extensive washing after the gold deposition.

Titanium (IV) oxide acetylacetonate (1.9651 g) was dissolved in methanol (500 cm³). Silica [Davison Grace 57 silica (>60 mesh), 60.01 g] was added to the titanium solution and rotated on a rotary evaporator for 2 h under nitrogen. The methanol was removed at 30° C. in vacuo. The dried materials were heated to 100° C. in vacuo. The solids were then dried at 120° C. in air over a weekend. The solids were calcined in air in a muffle furnace as follows: 110° C. to 600° C. in 3 h and held at 600° C. for 3 h to yield a support comprising titania dispersed on silica.

A gold solution was prepared as follows: Chloroauric acid ($HAuCl_4.3H_2O$, 0.3487 g) was dissolved in water (500 cm³) and heated to 70° C. An aqueous solution of sodium hydroxide (0.1 M) was added to the gold solution to adjust the pH to 8.8. The titania-containing support was added to the gold solution at 70° C. The resulting mixture was stirred for 1.5 h. The solids were settled, cooled to room temperature, then filtered. The solids were suspended in water (100 cm³) for 5 min, then filtered. The solids were dried at 120° C. for 6 h and then calcined in air as follows: 120° C. to 400° C. in 5 h and held a 400° C. for 3 h.

The catalyst (1 g) was loaded into a 10 cc fixed-bed, continuous flow reactor with flows of helium, oxygen, hydrogen, and propylene. Total flow rate was 150 cc/min (or GHSV 1,800 h$^{-1}$). Feedstream composition was 10 percent hydrogen, 10 percent oxygen, and 22 percent propylene, by volume, the balance being helium. Propylene, oxygen and helium were used as pure streams; hydrogen was mixed with helium in a 20 H$_2$/80 He (volume/volume) mixture. The pressure was atmospheric; reactor temperature was 140° C. Products were analyzed using an on-line gas chromatograph (Chrompack™ Poraplot™ S column, 25 m). The process was run for 1 h during which time the catalyst steadily deactivated. The hydro-oxidation process was shut down by shutting off the flows of propylene, oxygen, and hydrogen.

The deactivated catalyst was regenerated by a prior art method, namely, under a flow of oxygen (20 vol. percent), water (0.5 vol. percent), and helium (balance) for 45 min at 400° C. and atmospheric pressure. The regenerated catalyst was evaluated in the hydro-oxidation of propylene to propylene oxide at 140° C. and atmospheric pressure with the results shown in Table 1 (CE-1).

TABLE 1

Regeneration of Hydro-oxidation Catalyst
Au/TiO$_2$/SiO$_2$

| Example | Time on Stream (h) | PP Conv$^c$ (mol %) | PO Sel$^c$ (mol %) |
| --- | --- | --- | --- |
| CE-1$^a$ | 0.18 | 0.75 | 95.1 |
| | 0.35 | 0.56 | 97.9 |
| | 0.52 | 0.47 | 97.8 |
| | 0.68 | 0.43 | 98.0 |
| E-1$^b$ | 0.32 | 0.45 | 88.3 |
| | 0.48 | 0.44 | 95.0 |
| | 0.67 | 0.43 | 96.2 |

$^a$Deactivated catalyst regenerated for 45 min at 400° C. and atmospheric pressure in a stream of oxygen (20%), water (0.5%) and balance helium, by volume.
$^b$Deactivated catalyst regenerated for 2 h at 140° C. and atmospheric pressure in a stream of ozone (0.4%), oxygen (20%), water (0.5%), balance helium, by volume.
$^c$Hydro-oxidation process conditions: 10% hydrogen, 10% oxygen, 22% propylene, balance helium, by volume; GHSV, 1,800 h$^{-1}$; T, 140° C.; atmospheric pressure.
"PP Conv" is the mole percentage of propylene feed converted to products.
"PO Sel" is the mole percentage of converted propylene which forms propylene oxide.

It was found that the propylene conversion at 0.18 h after regeneration was 0.75 mole percent with a propylene oxide selectivity of 95.1 mole percent, the activity being close to the initial activity of the fresh catalyst. The percentage of propylene oxide in the effluent stream was 0.35 mole percent. At 0.68 h on stream after regeneration, the conversion was 0.43 mole percent with a selectivity of 98.0 mole percent. The catalyst was run for approximately 1 h, at which time the percentage of propylene oxide in the effluent stream had dropped to 0.10 mole percent, a reduction of 70 percent from the initial value after regeneration.

EXAMPLE 1

(E-1) Regeneration Method Using Ozone

The regenerated and then deactivated catalyst of Comparative Experiment CE-1 was regenerated a second time, this time by the method of the invention. Specifically, the deactivated catalyst was regenerated under a gaseous stream containing ozone (0.4 vol. percent), oxygen (20 vol. percent), water (0.5 vol. percent), balance helium. The regeneration stream was passed over the catalyst at 140° C. and atmospheric pressure for 1 h, after which the regeneration process was stopped. The regenerated catalyst was evaluated in the hydro-oxidation process at 140° C. and atmospheric pressure in the manner described in CE-1 with the results shown in Table 1, E-1. At 0.32 h on stream, the propylene oxide selectivity was 88.3 mole percent at a propylene conversion of 0.45 mole percent. At 0.48 h on stream, the propylene oxide selectivity was 95.0 mole percent at a propylene conversion of 0.44 mole percent. At 0.67 h on stream, the propylene oxide selectivity was 96.2 mole percent at a propylene conversion of 0.43 mole percent. The percentage of propylene oxide in the effluent stream was 0.26 mole percent.

When CE-1 was compared with E-1, it was found that the two regeneration methods produced regenerated catalysts with comparable activity and selectivity. Advantageously, the regeneration method of the invention, exemplified by E-1, which used ozone in addition to oxygen and water, was conducted at a lower temperature, as compared with the prior art regeneration method, CE-1, which used only oxygen and water. Accordingly, regeneration under ozone does not require high temperature cycling of the reactor.

EXAMPLE 2

Regeneration of a Hydro-Oxidation Catalyst Comparison of a Prior Art Method with the Method of the Invention A hydro-oxidation catalyst comprising gold, sodium, and magnesium on a support comprising titanium dispersed on silica was prepared in a similar manner to that described in Example 9 of international patent publication WO 98/00415, incorporated herein by reference.

Titanium isopropoxide (28.2 g) is dissolved in isopropanol (315 g) in a glovebox. The solution is placed into an addition funnel. Silica (PQ MS-1030) is wetted, dried at 110° C., and calcined at 500° C. A flask containing the silica (150 g) is attached to a rotary evaporator and cooled to 0° C. with an ice bath. The titanium isopropoxide solution is added to the silica in vacuo at 0° C. Solvent and volatiles are removed at 0° C. in vacuo. The residue is heated to room temperature in vacuo and rotated at room temperature for 30 min. The residue is heated to 50° C. in vacuo and rotated at 50° C. for 30 min, then heated to 80° C. in vacuo and rotated at 80° C. for 30 min. Finally, the residue is heated to 100° C. in vacuo and rotated at 100° C. for 30 min, and then calcined at 500° C. for 6 h in air yielding a support comprising titanium dispersed on silica.

A gold solution is made by dissolving chloroauric acid (8.86 g) into water (5120 cm³) and heating to 70° C. with agitation. The pH of the solution is adjusted slowly to 7.5 by adding dropwise an aqueous sodium carbonate solution (10 wt. percent). Magnesium nitrate (7.11 g) is added to the solution with agitation and the pH is readjusted with sodium carbonate to 7.5. The solution is cooled to 30° C. quickly. After 20 min the pH is 8.5. The support (150.0 g) is added quickly with stirring. The pH is readjusted to 7.5 with sodium carbonate solution. The mixture is maintained at 30° C. for 30 min while keeping the pH at 7.5. Then, the mixture is stirred for 2 h, and sodium carbonate solution is added when needed to maintain the pH at 7.5. The solids are filtered and washed with water (370 cm³) at pH between 7 and 8 (adjusted with sodium carbonate). The solids are oven dried at 110° C. for 12 h. The solids are calcined in air from room temperature to 110° C. in 30 min, from 110° C. to 700° C. in 5 h, held at 700° C. for 10 h, and then cooled to room temperature to obtain a catalyst comprising gold, sodium, and magnesium on a titanium-containing support.

The catalyst (10 g) was loaded into a fixed-bed, continuous flow reactor with flows of helium, oxygen, hydrogen, and propylene. Total flow rate was 2000 cm$^3$/min (or GHSV 6,000 h$^{-1}$). Feedstream composition was 7 percent hydrogen, 7 percent oxygen, and 20 percent propylene, by volume, the balance being helium. Propylene, oxygen and helium were used as pure streams; hydrogen was mixed with helium in a 20 H$_2$/80 He (volume/volume) mixture. The pressure was 200 psig (1,379 kPa); reactor temperature was 160° C. Products were analyzed using an on-line mass spectrometer. The process was run for 1 h, at which time the mole percentage of propylene oxide in the effluent stream had decreased to about 50 percent of its initial value. The hydro-oxidation process was shut down by shutting off the flows of propylene, oxygen, and hydrogen.

The deactivated catalyst was regenerated by a prior art method, namely, under a flow of oxygen (20 vol. percent), water (0.5 vol. percent), and helium (balance) for 6 h at 375° C. and a total pressure of 200 psig (1,379 kPa). The regenerated catalyst was evaluated in the hydro-oxidation of propylene to propylene oxide at 160° C. and 200 psig. It was found that the maximum propylene conversion was 1.82 mole percent with a propylene oxide selectivity of 89.4 mole percent. (Table 2, CE-2-A).

When the regenerated catalyst exhibited reduced activity in the hydro-oxidation process, measured by a 67 percent reduction in the mole percentage of propylene oxide in the effluent stream as compared with the initial regenerated value, the hydro-oxidation process was again shut down. The deactivated catalyst was regenerated a second time, this time by the method of the invention, namely, under a gaseous stream containing ozone (0.4 vol. percent), oxygen (20 vol. percent), water (0.5 vol. percent), and helium (balance). The regeneration stream was passed over the catalyst at 160° C. and atmospheric pressure for 1 h, after which time the regeneration process was stopped. The twice regenerated catalyst was evaluated in the hydro-oxidation process at 160° C. and 200 psig (1,379 kPa) with the results shown in Table 2 (E-2-A).

When the twice regenerated catalyst had lost significant activity in the hydro-oxidation process, taken as a 37 mole percent reduction of propylene oxide in the effluent stream, the deactivated catalyst was regenerated a third time using the ozone treatment of the invention, described above. The thrice regenerated catalyst was evaluated in the hydro-oxidation process with the results shown in Table 2 (E-2-B). The hydro-oxidation process was run until the catalyst showed substantial deactivation, as measured by a 50 percent reduction of propylene oxide in the effluent stream.

The regeneration and hydro-oxidation processes were repeated a fourth time using the aforementioned regeneration conditions of the prior art with the results shown Table 2 (CE-2-B). Again, the hydro-oxidation process was run until the catalyst lost about 50 percent of its initial regenerated activity.

The regeneration process and hydro-oxidation process were repeated a fifth, sixth, and seventh time using the regeneration conditions of this invention. See Table 2 (E-2-C, D, E).

An eighth cycle was repeated using the regeneration conditions of the prior art, with the exception that the regeneration time was only 0.5 h. See Table 2 (CE-2-C).

A ninth cycle was repeated using the regeneration conditions of the prior art, using the 6 h regeneration time. See Table 2 (CE-2-D).

A tenth cycle was repeated using the regeneration conditions of the invention, with the exception that the regeneration was conducted for 3 h, instead of 1 h. See Table 2 (E-2-F).

TABLE 2

Regeneration of Hydro-Oxidation Catalyst
Prior Art Method versus Method of the Invention

| Run | Feed$^{a,b}$ | T (° C.) | P (psi) | h | PP Conv$^c$ (mol %) | PO Sel$^c$ (mol %) |
|---|---|---|---|---|---|---|
| CE-2-A | O$_2$/H$_2$O | 375 | 200 | 6 | 1.82 | 89.4 |
| E-2-A | O$_3$/O$_2$/H$_2$O | 160 | 14.6 | 1 | 1.47 | 84.0 |
| E-2-B | O$_3$/O$_2$/H$_2$O | 160 | 14.6 | 1 | 1.46 | 82.4 |
| CE-2-B | O$_2$/H$_2$O | 375 | 200 | 6 | 1.99 | 91.9 |
| E-2-C | O$_3$/O$_2$/H$_2$O | 160 | 14.6 | 1 | 1.75 | 90.3 |
| E-2-D | O$_3$/O$_2$/H$_2$O | 160 | 14.6 | 1 | 1.67 | 89.1 |
| E-2-E | O$_3$/O$_2$/H$_2$O | 160 | 14.6 | 1 | 1.54 | 89.0 |
| CE-2-C | O$_2$/H$_2$O | 375 | 200 | 0.5 | 1.64 | 91.8 |
| CE-2-D | O$_2$/H$_2$O | 375 | 200 | 6 | 1.99 | 93.4 |
| E-2-F | O$_3$/O$_2$/H$_2$O | 160 | 14.6 | 3 | 1.94 | 92.7 |

$^a$·Feed containing no ozone: oxygen (20%), water (0.5%), balance helium, by volume.
$^b$·Feed containing ozone: ozone (0.4%), oxygen (20%), water (0.5%), balance helium, by volume.
$^c$·Hydro-oxidation process conditions: 7% hydrogen, 7% oxygen, 20% propylene, balance helium, by volume: GHSV, 6,000 h$^{-1}$; T, 160° C.: P. 200 psig. "PP Conv" is the mole percentage of propylene feed converted to products. "PO Sel" is the mole percentage of converted propylene which forms propylene oxide.

It can be seen from Table 2 that a catalyst regenerated by the method of the invention, which used ozone, produced a regenerated catalyst with comparable activity and selectivity to the catalyst regenerated by prior art methods, which did not use ozone. More advantageously, the regeneration method of the invention achieved the same results at a lower temperature and over a shorter time, as compared with the prior art method.

What is claimed is:

1. A process of activating or regenerating a hydro-oxidation catalyst comprising contacting a fresh hydro-oxidation catalyst or a deactivated hydro-oxidation catalyst with an ozone stream, the hydro-oxidation catalyst comprising one or more catalytic metals deposited on a catalyst support, the contacting being conducted under process conditions sufficient to activate the fresh hydro-oxidation catalyst or regenerate, at least in part, the deactivated hydro-oxidation catalyst in a hydro-oxidation process wherein a hydrocarbon is oxidized with oxygen in the presence of hydrogen to form a partially-oxidized hydrocarbon.

2. The process of claim 1 wherein the ozone stream comprises one or more diluents.

3. The process of claim 2 wherein the diluent is selected from the group consisting of oxygen, nitrogen, water, carbon dioxide, air, helium, argon, and mixtures thereof.

4. The process of claim 2 wherein ozone comprises from greater than about 0.05 to less than about 20 volume percent of the ozone stream.

5. The process of claim 1 wherein the gas hourly space velocity of the ozone stream is greater than about 0.1 h$^{-1}$ and less than about 1,000 h$^{-1}$.

6. The process of claim 1 wherein the temperature is greater than about 20° C. and less than about 250° C.

7. The process of claim 1 wherein the pressure is greater than about 7 psia (48 kPa) and less than about 100 psia (690 kPa).

8. The process of claim 1 wherein the activation or regeneration process is effected for a time greater than about 15 minutes and less than about 6 hours.

9. The process of claim 1 wherein the hydro-oxidation catalyst comprises one or more catalytic metals selected from gold, silver, the platinum group metals, the lanthanide metals, and combinations thereof, on a catalytic support.

10. The process of claim 9 wherein the total loading of catalytic metals on the support is greater than about 0.005 and less than about 20 weight percent, based on the total weight of the catalyst.

11. The process of claim 9 wherein the catalytic support is selected from titanium-containing supports, vanadium-containing supports, and zirconium-containing supports.

12. The process of claim 1 wherein the hydro-oxidation catalyst comprises gold, or silver, or combinations of gold and silver, on a titanium-containing support.

13. The process of claim 12 wherein the total loading of gold and silver on the titanium-containing support is greater than about 0.005 and less than about 20 weight percent, based on the total weight of the catalyst.

14. The process of claim 12 wherein the titanium-containing support is selected from the group consisting of titanium dioxide, titanosilicates, promoter metal titanates, titanium dispersed on silica, titanium dispersed on promoter metal silicates, and supports containing extra-framework, non-framework, and grafted titanium, and mixtures thereof.

15. The process of claim 12 wherein the catalyst further comprises a promoter metal.

16. The process of claim 15 wherein the promoter metal is selected from the group consisting of Group 1, Group 2, the platinum group metals, the lanthanide re earth metals, and the actinide metals of the Periodic Table, and mixtures thereof.

17. The process of claim 15 wherein the promoter metal is selected from lithium, sodium, potassium, rubidium, cesium, magnesium, calcium, barium, erbium, lutetium, and combinations thereof.

18. The process of claim 12 wherein the catalyst comprises gold but not silver.

19. The process of claim 12 wherein the catalyst comprises silver but not gold.

20. The process of claim 12 wherein the catalyst comprises silver and gold.

21. The process of claim 12 wherein the hydro-oxidation catalyst is used in a process of oxidizing a $C_{3-12}$ olefin with oxygen in the presence of hydrogen to form an olefin oxide.

22. The process of claim 21 wherein the olefin is propylene.

23. The process of claim 1 wherein the ozone stream comprises ozone and oxygen.

24. The process of claim 23 wherein the ozone stream further comprises water.

25. The process of claim 1 wherein the hydro-oxidation catalyst is used in a process of oxidizing an olefin with oxygen in the presence of hydrogen to form an olefin oxide.

26. The process of claim 25 wherein the olefin is a $C_{3-12}$ olefin.

27. The process of claim 1 wherein the hydro-oxidation catalyst is used in a process of oxidizing an alkane with oxygen in the presence of hydrogen to form an alcohol or a ketone.

28. A process of activating or regenerating a hydro-oxidation catalyst comprising contacting a fresh hydro-oxidation catalyst or a deactivated hydro-oxidation catalyst with a stream comprising ozone and, optionally, oxygen, the hydro-oxidation catalyst comprising gold and at least one promoter metal selected from the group consisting of lithium, sodium, potassium, rubidium, cesium, magnesium, calcium, barium, erbium, and lutetium deposited on titanosilicate, the contacting being conducted under process conditions sufficient to activate the fresh hydro-oxidation catalyst or regenerate, at least in part, the deactivated hydro-oxidation catalyst in a hydro-oxidation process wherein propylene is oxidized with oxygen in the presence of hydrogen to form propylene oxide.

* * * * *